United States Patent [19]

Leoncavallo

[11] Patent Number: 4,772,418
[45] Date of Patent: Sep. 20, 1988

[54] AUTOCLAVABLE RACK CONTAINER

[75] Inventor: Richard A. Leoncavallo, Pittsford, N.Y.

[73] Assignee: Nalge Company, Rochester, N.Y.

[21] Appl. No.: 913,912

[22] Filed: Oct. 1, 1986

[51] Int. Cl.$^4$ ............................................. A61L 2/06
[52] U.S. Cl. ..................................... 422/310; 422/26; 422/297; 422/300; 206/508; 220/380
[58] Field of Search ................. 422/26, 297, 300, 310; 436/1; 206/438, 439, 508, 509, 512; 220/366, 380, 335, 290; 435/293, 297, 301

[56] References Cited

U.S. PATENT DOCUMENTS

| 3,651,981 | 3/1972 | Kinney | 220/366 X |
| 3,961,603 | 6/1976 | Gaddie, Sr. | 220/380 X |
| 4,154,795 | 5/1979 | Thorne | 422/102 X |
| 4,358,908 | 11/1982 | Song | 220/366 X |
| 4,495,289 | 1/1985 | Lyman et al. | 435/300 X |
| 4,512,498 | 4/1985 | Leibinger | 220/366 X |
| 4,551,311 | 11/1985 | Lorenz | 422/300 |
| 4,576,309 | 3/1986 | Tzifkansy et al. | 220/366 |
| 4,577,760 | 3/1986 | Rainin et al. | 220/366 X |
| 4,584,182 | 4/1986 | Sanderson et al. | 422/26 X |

OTHER PUBLICATIONS

The American V. Mueller Sterilization Container System, American Hospital Supply Corporation, 1984.

Primary Examiner—Barry S. Richman
Assistant Examiner—Lynn M. Kummert
Attorney, Agent, or Firm—Marjama & Pincelli

[57] ABSTRACT

A container comprising a top cover for placement on a base support. The top cover may be placed in a first position on the base support to allow steam or gas to enter within the container and a second position for providing a seal between the cover and base support.

4 Claims, 5 Drawing Sheets

AUTOCLAVABLE RACK CONTAINER

The present invention is directed to an autoclavable container having a supporting rack therein, more particular to an improved autoclavable plastic container for holding a pipet tip.

BACKGROUND OF THE INVENTION

Pipet tips are normally sold in containers having a shelf therein having a plurality of openings for receiving and holding pipet tips. While pipet tips may be purchased in sterilized packs, it is important to the user to assure sterilization of the pipet tips prior to use. For this reason the pipet tips may again be sterilized before use. Additionally, in many procedures not all the pipet tips are used and therefore the remaining tips are required to be resterilized before use. In the prior art, pipet tip containers are normally placed in an autoclave and the cover loosely put on top of the tips such that at least some of the tips are exposed to the sterilization environment in which it is placed. This type of positioning results in the possibility that liquid moisture may condense in some of the pipet tips or in the container itself which could later present problems with regard to contamination of the pipet tips. After autoclaving the container is removed and the cover is lifted and repositioned upon the container in a sealed position. This later movement presents the possibility of contaminating the pipet tips due to the movement of the air surrounding the pipet tips.

Applicants have invented an improved container particularly adapted for holding pipet tips such that pipet tips may be sterilized which avoid or minimize the problems of the prior art.

SUMMARY OF THE PRESENT INVENTION

The present invention is directed to a container having a top cover having a continuous outer peripheral wall which terminates in a rim portion. The top cover is placed over a base support which has a continuous upstanding peripheral wall which terminates at its upper end in a ridge portion. The ridge portion mates with the rim portion of the cover. The base support is provided with a shelf for receiving and holding a plurality of pipet tips therein. Means are provided for maintaining said top cover in an unsealed position during autoclaving which will allow steam or gas to enter within the container so as to sterilize the pipet tips.

DETAILED DESCRIPTION OF THE DRAWINGS

Figure 1:
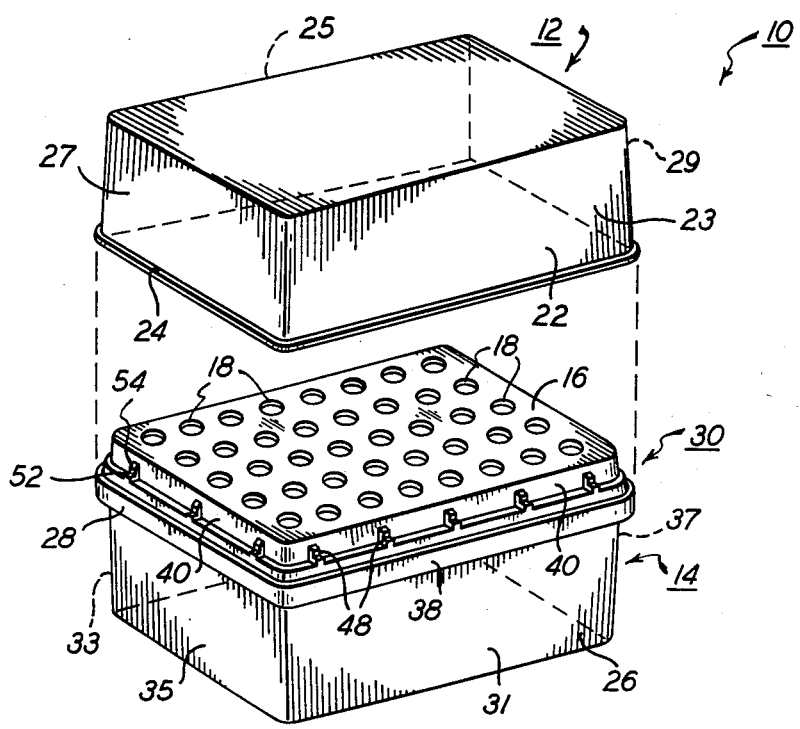
FIG. 1 is an exploded perspective view of a container made in accordance with the present invention.
Figure 2:
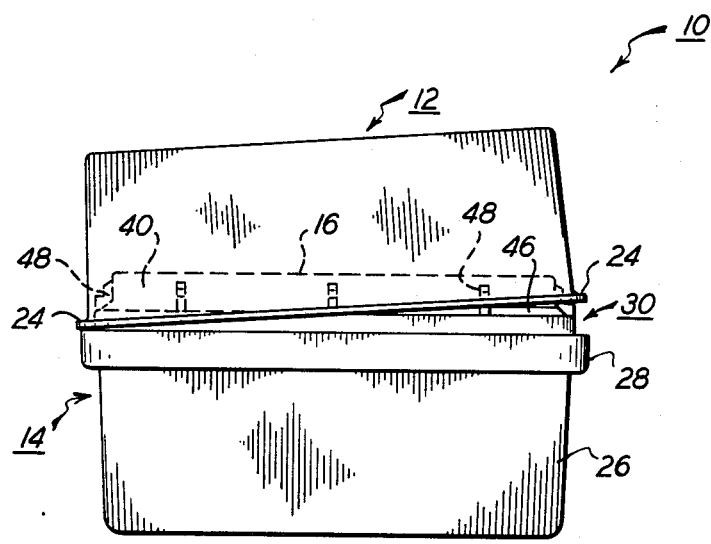
FIG. 2 is an end view of the container of FIG. 1 showing the cover in the unsealed position.
Figure 2A:
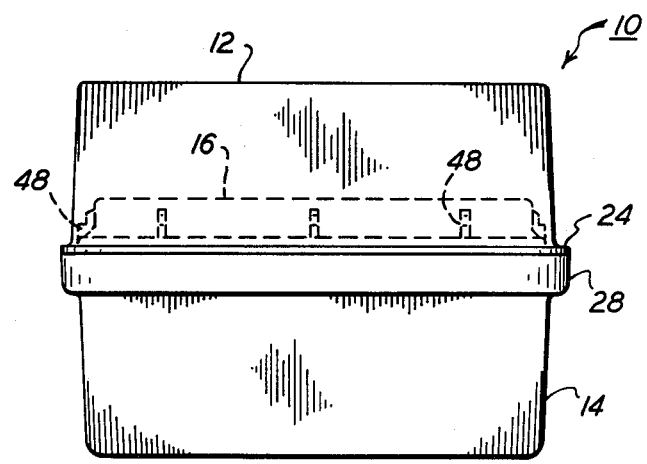
FIG. 2A illustrates the container of FIG. 2 in the sealed position.
Figure 3:
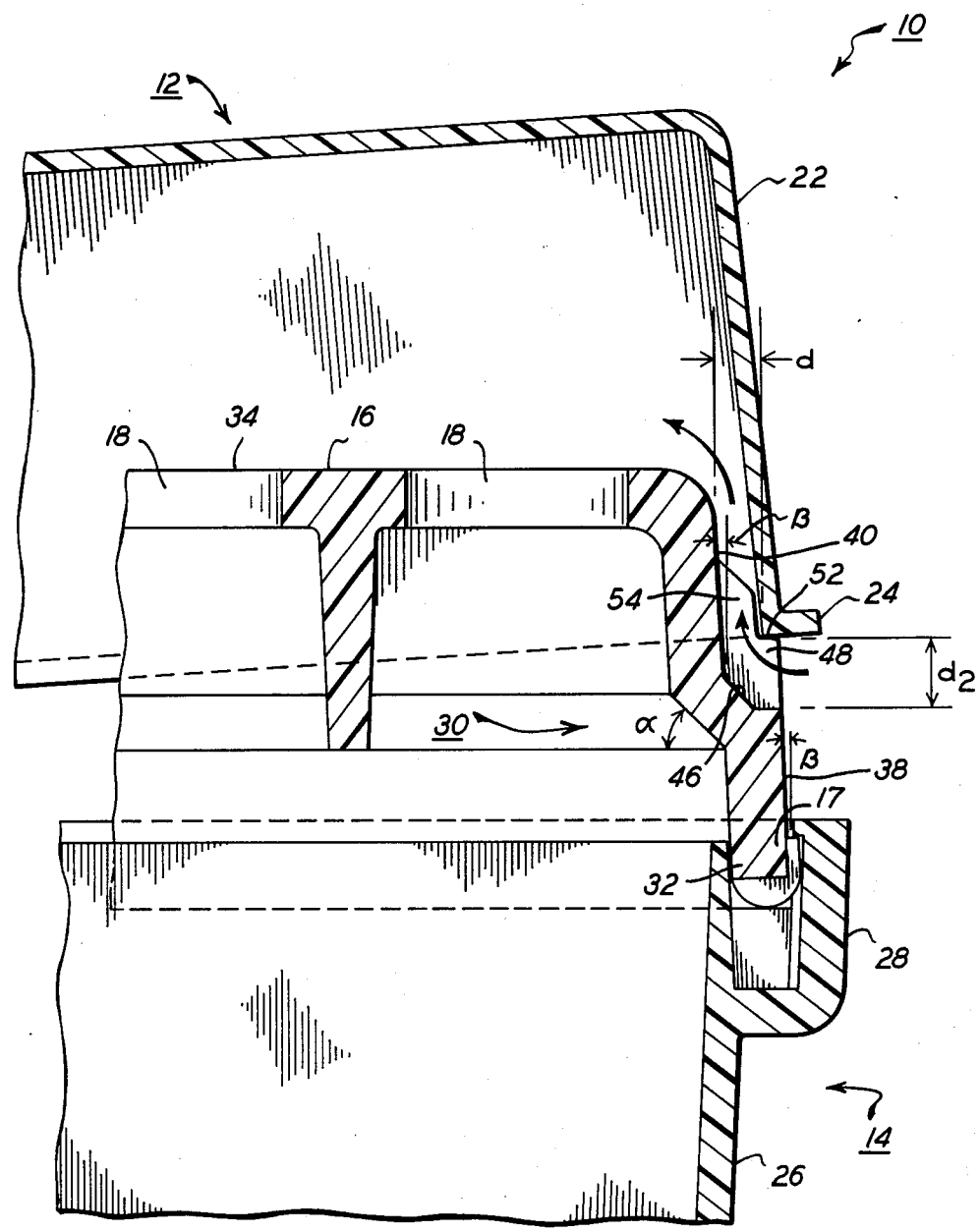
FIG. 3 is an enlarged fragmentary cross-sectional view of that portion circled in FIG. 2.

Referring to FIGS. 1, 2 and 3 there is illustrated a container 10 made in accordance with the present invention. The container 10 comprises a top cover 12 which is placed over base support 14. The base support 14 has a shelf 16 secured thereto. The shelf 16 is provided with a plurality of openings 18. Each opening 18 is designed to receive a pipet tip (not shown). In FIGS. 2, 3, 4, 5 and 7 the container 10 is illustrated in the unsealed position wherein the top cover 12 is placed such that steam and/or gas is allowed to flow within the container so as to sterilize pipet tips placed therein. Illustrated in FIG. 2A the top cover 12 is shown in the closed position.

Figure 5:
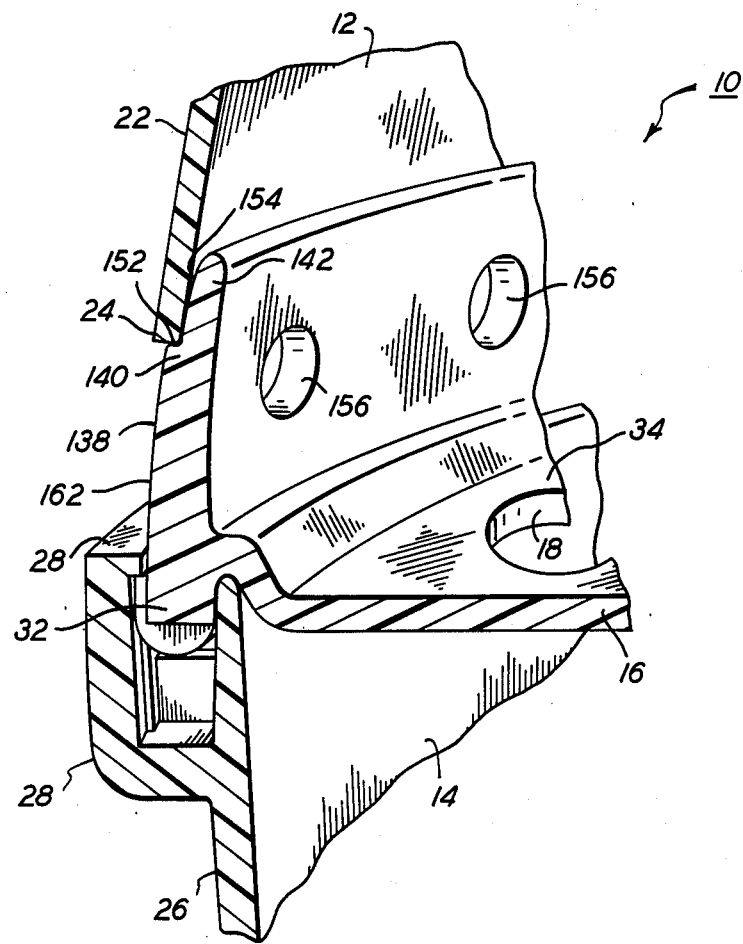
FIG. 5 is a view similar to FIG. 3 illustrating a modified form of the present invention.

Referring to FIG. 3 there is illustrated an enlarged fragmentary view of the container of FIG. 2 illustrating the means used to position the cover in a secure unsealed position during autoclaving. The top cover 12 has a continuous outer peripheral wall 22 which terminates at its lower end in a rim portion 24. In the particular embodiment illustrated, rim portion 24 preferably has a substantially L-shaped cross section, however, the present invention is not limited to such cross section. The rim portion 24 may simply be the straight extension of wall 22 as illustrated in FIG. 5. The base support 14 comprises a continuous upstanding outer peripheral wall 26 which terminates at its upper end in a ridge portion 28 which mates with rim portion 24 of top cover 12. In the particular embodiment illustrated, the container has an overall rectangular configuration such that the outer peripheral wall 22 has two opposed long sides 23, 25 and two opposed short sides 27, 29. The base support 14 is similarly constructed such that outer peripheral wall 26 has opposed long sides 31, 33 and opposed short sides 35, 37. While the embodiment illustrated is rectangular, the container may take other desired configurations, for example, square, circular or oval.

The shelf 16 comprises a substantially vertically upstanding wall 30 having its lower end 32 secured to the ridge portion 28 of base support 14. In the particular embodiment illustrated, end 32 snaps into ridge portion 28, however, end 32 may be secured in any desired manner to base support 14. If desired the shelf 16 may be integrally formed with the base support 14. The vertical wall 30 terminates at its upper end in the support surface 34 which extends across the shelf wherein the openings 18 are provided. In the particular embodiment illustrated, each opening 18 is designed to receive an individual pipet tip. It is, of course, understood that the arrangements of the openings and the number of openings may be selected as desired. Vertically upstanding wall 30 comprises a first upstanding wall portion 38 which extends for at least a portion about the periphery of said shelf. In the particular embodiment illustrated, first upstanding wall portion 38 extends about the entire periphery. Upstanding wall 30 is also provided with a second upstanding wall portion 40 which forms the upper end thereof which merges into support surface 34. Second upstanding wall portion 40 is disposed axially inwardly of said first upstanding wall portion 38. The lower end of second upstanding wall 40 is connected to first vertical wall portion 38 by connecting portion 46 at its juncture. The connecting portion 46 is disposed at an angle α of approximately 45° with respect to the horizontal plane. However, the connecting portion can be disposed at any desired angle α so as to provide the appropriate axial displacement between second upstanding wall 40 with respect to first upstanding wall portion 38. First upstanding wall portion 38 and second upstanding wall 40 are preferably slanted axially inward at a small angle β with respect to the vertical plane to facilitate placing of the cover on the base support. The angle β is generally in the range of one to ten degrees (1°–10°), preferably in the range of one to five degrees (1°–5°) and in the particular embodiment illustrated, is about three degrees (3°). A plurality of ribs 48 are spaced about the periphery on the outer surface of wall 40. In the particular embodiment illustrated, approximately five (5) ribs 48 are disposed along the long sides of wall 40. However, any desired number may be provided. Each rib 48 is designed so as to provide a first vertical supporting surface 52 for supporting the rim portion of the cover 24. The surface 52 is spaced a distance $d_2$ from the base of rib 48. While in the embodiment illustrated, ribs 48 are shown on all sides of the shelf 16, ribs 48 need only be placed on at least one side to support a portion of the cover 12. Preferably the ribs are placed on both long sides of shelf 16 such that the ribs 48 on either side may support the cover. In the unsealed position, the long side 25 of cover 12 is placed on ridge portion 28 on the long side 33 of base 14 and the long side 23 of cover 12 is placed on surface 52 of rib 48 is on upstanding wall 30 adjacent thereto. Each rib is provided with an axial supporting surface 54 for spacing the inside surface of the cover 12 away from the outer surface of wall 40 of shelf 16. In this manner steam or gas may pass between the shelf and cover as illustrated by the arrows. The particular dimensional spacing d between axial supporting surface 54 and outer surface 48 may vary as desired so long as sufficient space is provided for passage of steam or gas between the cover and shelf. In the particular embodiment illustrated the axially spaced surface 54 is spaced a distance d of approximately 0.05 inches from the outer surface and vertical support surface 52 is disposed a distance $d_2$ of approximately 0.06 inches from the base of rib 48. In the practice of the present invention, the ribs 48 need only be placed on one wall 40, however, since the cover may be placed a variety of different ways, as previously discussed, ribs 48 are preferably placed on all the sides.

Figure 4:
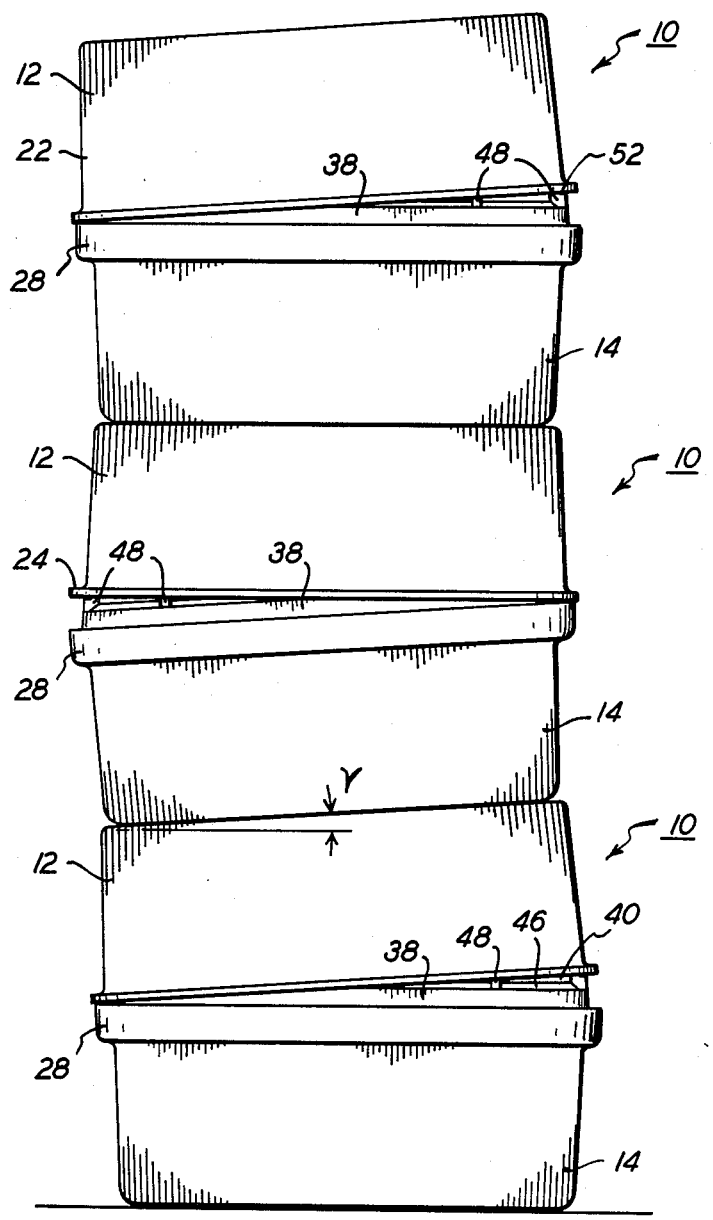
FIG. 4 is a side view illustrating how several containers made in accordance with the present invention may be stacked upon each other during autoclaving.

The top cover is designed such that the rim portions of opposed sides of the outer peripheral wall 22 are spaced apart a distance such that one side rests on ridge portion 28 and the other on supporting surface 52 of rib 48 in the unsealed position (as shown in FIG. 4) and when in the sealed position the sides press snugly against the lower end of the adjacent wall 30 (see FIG. 2A). The container 10 is made of a generally flexible material which can maintain a preformed shape. In the particular embodiment illustrated, container 10 is made of plastic, more particularly of a polystyrene.

In using the container in the present invention the container is first filled with pipet tips in their respective openings 18. Thereafter the cover 12 is placed on the base support 14 as illustrated in FIG. 2 after which the container is placed in an autoclave where it is sterilized, preferably by steam. As illustrated in FIG. 2, the size and dimensional spacing of the rib is such that there is a relatively low angle γ between the top surface of the cover and the horizontal which allows a plurality of containers containing pipet tips to be stacked as illustrated in FIG. 4 during sterilization. Generally angle γ is from about two to ten degrees (2°–10°), preferably from about three to five degrees (3°–5°) and in the particular embodiment illustrated, angle β is five degrees (5°). After sterilization the cover 10 is simply pushed down and sealed as illustrated in FIG. 2A wherein the inside surface of rim portion 24 forms a sealing relationship with the lower end of the outer surface of first upstanding wall 38 and the top of ridge portion 28. As previously discussed, the cover 12 is preferably made of a plastic material which provides a rigid shape yet is still flexible enough so as to be easily pushed down into sealing engagement. Mounting the cover 12 in the position illustrated during sterilization has the advantage of minimizing, if not preventing, the condensation of moisture in the container or in the pipet tips. Additionally, the closure of the top cover is accomplished in one quick single action wherein air will most likely be forced out from underneath the cover thereby minimizing, if not eliminating, any potential contamination of the pipet tips that may be caused by lifting and moving the cover separately upon the structure as in the prior art.

Figure 7:
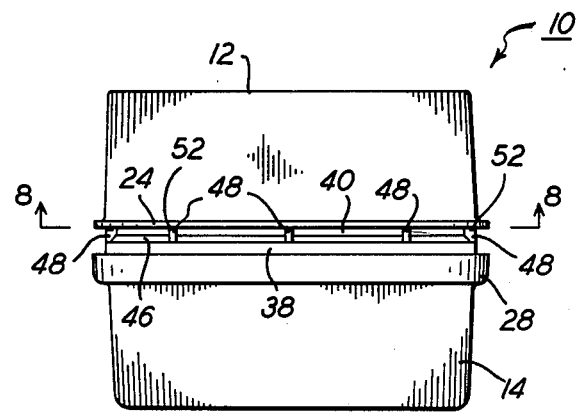
FIG. 7 is an end view of the container of FIG. 1 showing the cover in an alternate unsealed position.
Figure 8:
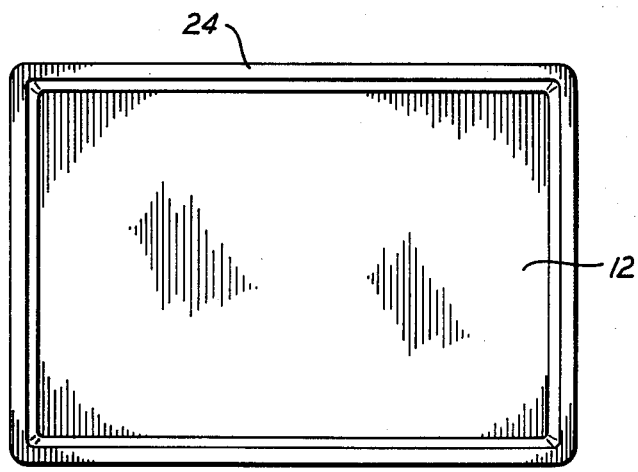
FIG. 8 is a bottom view of the cover of FIG. 7 in the preformed enlarged state.

While in the preferred embodiment the cover 12 in the unsealed position is placed on the lower base support 14 as shown in FIGS. 2 and 4, the top cover 12 may be positioned such that all sides 23, 25, 27 and 29 rest upon ribs 48 as illustrated in FIG. 7. The top cover 12, when designed for positioning in this mode, is preferably shaped so that the sides are slightly concave in its shape as illustrated in FIG. 8 so that opposed sides are closer to each other. This allows the cover to exert pressure on the ribs to more securely maintain the cover on the shelf during autoclaving. The cover 12 would seal in the same manner as previously discussed by simply packing the cover directly down on the base support 14.

Referring to FIG. 5 there is illustrated a fragmentary view similar to FIG. 3 of a modified form of the present invention. In the embodiment illustrated, like numerals indicate similar parts as previously discussed with regard to the embodiments illustrated in FIGS. 1 through 4. In this embodiment container 10 has a top cover 12 and base support 14, the top cover 12 having a continuous outer peripheral wall 22 which terminates in rim portion 24. The base support 14 has a continuous upstanding outer peripheral wall 26 which terminates in ridge portion 28. Base portion 14 is also provided with a shelf 16 which has a support surface 34 and a plurality of openings 18 therein for receiving pipet tips. The shelf 16 has a mating portion 32 which locks into rim portion 28. Shelf 16 has a first upstanding wall portion 138 having an upper end 140. Extending from the juncture of upper end is a second wall 142 which extends about at least a portion of the wall 138. Wall 142 is disposed axially inward of first upstanding wall 138 so as to provide a vertical support surface 152 for supporting rim portion 24 of top cover 12 and an axial surface 154 to mate with the inside surface of outer peripheral wall 22 of top cover 12. The top cover in the position illustrated in FIG. 5 is in the unsealed position for use during autoclaving of the container and pipet tips. The first upstanding wall 138 is provided with at least one opening 156 therein below vertical support surfaces 152 to allow ingress and egress of steam or gas during autoclaving of the container. The top cover is sealed in the same manner presently discussed with respect to FIGS. 1–4. The inside surface of rim portion 24 mates with the lower end 162 of first upstanding wall 138 and ridge portion 28 so as to effectively seal the cover on the container. In the particular embodiment illustrated in FIG. 5 the second upstanding wall 142 is shown as being continuous about its length. However, wall 142 may be broken up into a plurality of spaced substantially vertically extending independent projections (not shown). Additionally, the openings 156 may be disposed in any desired location so as to provide ingress and egress of air within the container during autoclaving, In this embodiment as in the previous embodiment discussed, the cover is placed on base support and closed in the same manner. Because of the flexibility of the cover, i.e., being made of plastic, the cover easily expands to allow being pushed down into mating relationship with the base.

Figure 6:
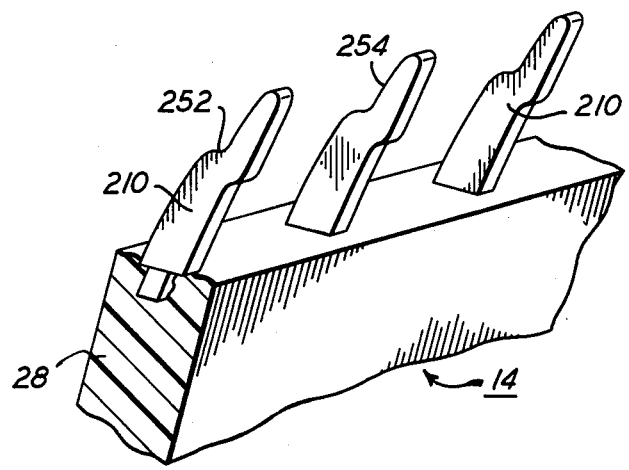
FIG. 6 is a view similar to FIG. 3 illustrating yet another modified form of the present invention.

Referring to FIG. 6 there is illustrated a fragmentary view similar to FIG. 3 of yet another modified form of the present invention. This embodiment is similar to that illustrated in FIG. 5, however, instead of having a single continuous first outer wall portion there is provided a plurality of independently spaced substantially vertically extending projections 210 spaced at least a portion of one side of the shelf. The projections 210 are each provided with a first vertical support 252 and axial support 254 mating with the lower end of the top cover 12 in the same manner previously discussed in the embodiment of FIG. 5. Here again, elements having the identical numbers illustrated in FIGS. 1 to 4 indicate identical parts.

What is claimed is:

1. A container for supporting pipet tips comprising a top cover having a continuous outer peripheral wall which terminates in a rim portion, a base support having a bottom surface and a continuous upstanding outer peripheral wall extending from said bottom surface which terminates in a ridge portion, said base support having a shelf disposed therein which is spaced from said bottom surface, said shelf having an outer periphery, a plurality of openings, and support means positioned and arranged on said outer periphery for maintaining said top cover in a first unsealed position so as to allow steam or gas to enter said container, each of said openings being positioned and arranged to support a pipet tip, said support means being positioned and arranged to permit said top cover to be pushed directly down to a second position from said first unsealed position so as to seal said container, said support means for maintaining said top cover in said first unsealed position comprising a first upstanding wall which extends about at least a portion of the outer periphery of said shelf and terminates in an upper end portion, a second substantially upstanding wall extending from said upper end portion of said first upstanding wall and disposed substantially axially inward from said upper end so as to form a juncture, a plurality of spaced ribs or projections extending from said juncture along said second upstanding wall a predetermined distance, said plurality of spaced ribs having a supporting surface positioned and arranged for supporting said rim portion of said top cover, said plurality of spaced ribs forming a plurality of passageways therebetween for allowing steam or gas to pass between said top cover and said shelf.

2. A container according to claim 1 wherein said continuous outer peripheral wall has a pair of opposed sides which are spaced apart a predetermined distance, said predetermined distance is such that when one side of the top cover is on said continuous upstanding outer peripheral wall of said support base, said top cover is maintained in said first unsealed position.

3. An autoclavable container for supporting pipet tips comprising:

a cover having a peripheral rim;

a base support having a bottom surface and a continuous upstanding peripheral wall extending from said bottom surface which terminates in a ridge, said base support including a support shelf spaced from said bottom surface, said shelf having an outer periphery, a plurality of openings and a first upstanding wall having a terminal end, each of said openings positioned and arranged to support a pipet tip, said first upstanding wall extending substantially continuously about the outer periphery of said shelf, a second substantially vertically upstanding wall extending from the terminal end of said first upstanding wall about at least a portion of the periphery of said shelf axially inward of said first upstanding wall forming a juncture therebetween, said second substantially vertically upstanding wall having a peripheral support means positioned and arranged for maintaining at least a portion of said cover at a first spaced position from said ridge of said base support so as to provide easy flow of gas or steam between said cover and said shelf to within said container, and support means comprising a plurality of ribs spaced about the periphery of said second substantially vertically upstanding wall at said juncture which extends along at least a portion of said second vertical wall, each of said plurality of ribs being provided with a first horizontal support ridge spaced a distance from said juncture positioned and arranged for supporting at least a portion of said rim of said cover and a vertical wall positioned and arranged for providing an axial stop to prevent further axially inward deflection of said rim portion of said cover, said support means being positioned and arranged to permit said top cover to be pushed directly down to a second position from said first unsealed position so as to seal said container.

4. A container according to claim 3 wherein said top cover has a substantially rectangular shape comprising four outer wall sections, said outer wall sections being constructed such that each of said outer wall sections is concave so as to be closer together when not in mating relationship with the base support, the axial space between the opposed wall sections of said cover is equal to or less than the distance between said first upstanding walls on said shelf with which said side wall sections are designed to mate.

* * * * *